United States Patent [19]

Huellmann et al.

[11] Patent Number: 4,965,376
[45] Date of Patent: Oct. 23, 1990

[54] 3,9-DIHYDROXYNONYNE AND ITS DERIVATIVES PROTECTED AT THE 9-OH FUNCTION

[75] Inventors: Michael Huellmann, Heppenheim; Rainer Becker, Bad Durkheim; Gerald Lauterbach, Ludwigshafen; Ernst Buschmann, Ludwigshafen; Heinz Eckhardt, Ludwigshafen; Walter Himmele, Walldorf; Christiane Brueckner, Ludwigshafen, all of Fed. Rep. of Germany

[73] Assignee: BASF Aktiengesellschaft, Ludwigshafen, Fed. Rep. of Germany

[21] Appl. No.: 340,035

[22] Filed: Apr. 18, 1989

[30] Foreign Application Priority Data

May 4, 1988 [DE] Fed. Rep. of Germany ....... 3815043

[51] Int. Cl.$^5$ .................. C07D 309/12; C07C 33/044
[52] U.S. Cl. .................................... 549/423; 556/449; 560/112; 560/262; 568/597; 568/662; 568/675; 568/855
[58] Field of Search ............... 568/855, 675, 597, 662; 549/423; 556/449; 560/112, 262

[56] References Cited

U.S. PATENT DOCUMENTS 3,845,108  10/1974  Roelofs ............................. 560/261

FOREIGN PATENT DOCUMENTS 2098609  11/1982  United Kingdom .

Primary Examiner—Nicky Chan
Attorney, Agent, or Firm—Oblon, Spivak, McClelland, Maier & Neustadt

[57] ABSTRACT

3,9-Dihydroxynonyne and its derivatives protected at the 9-OH function, of the general formula I

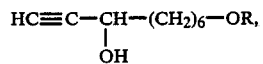

where R is hydrogen or a conventional alcohol protective group, and processes for the preparation of the compounds I.

2 Claims, No Drawings

3,9-DIHYDROXYNONYNE AND ITS DERIVATIVES PROTECTED AT THE 9-OH FUNCTION

The present invention relates to 3,9-dihydroxynonyne and its derivatives protected at the 9-OH function, of the general formula I

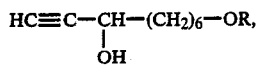    I where R is hydrogen or a conventional base-stable alcohol protective group.

The novel compounds I are used as intermediates for the synthesis of E-7, Z-9-dodecadienyl acetate, the pheromone of the grape berry moth, Lobesia botrana. This pheromone was first described in 1973, for example in US-A-3 845 108.

The preparation process stated there has 10 generally expensive process steps and is thus very involved. It is unsuitable for the synthesis of relatively large amounts, as required for the use of pheromone active ingredients for insect control over large areas by the confusion method.

It is an object of the present invention to provide a cheap, technically simple preparation process for the pheromone active ingredient.

We have found that this object is achieved by the provision of the novel 3,9-dihydroxynonyne or its derivatives protected at the 9-OH function (formula I), which are described at the outset.

Suitable protective groups R are base-stable hydroxyl protective groups, for example $C_4$-$C_{20}$-tert-alkyl, in particular $C_4$-$C_{12}$-tert-alkyl, groups which carry a tertiary carbon atom in the 1-position, such as tert-butyl, 1,1-dimethylprop-1-yl, 1,1-dimethylbut-1yl, 1,1,2-trimethylprop-1-yl, 1,1-dimethylpent-1-yl, 1,1,2-trimethylbut-1-yl, 1,1,3-trimethylbut-1-yl, 1-ethyl-1-methylbut-1-yl, 1,1-dimethylhex-1-yl and 1,1-dimethyl-2-ethylbut-1-yl; $C_3$-$C_{20}$-trialkylsilyl groups, preferably $C_3$-$C_8$-trialkylsilyl groups, such as trimethylsilyl, triethylsilyl, tri-n-propylsilyl, triisopropylsilyl, tri-n-butylsilyl, dimethylethylsilyl, diethylmethylsilyl, dimethyl-n-propylsilyl, dimethylisopropylsilyl, dimethyl-n-butylsilyl and dimethyl-tert-butylsilyl; benzyl; benzoyl; $C_2$-$C_{10}$-acyl groups, for example alkanoyl groups, such as acetyl, propionyl and butyryl; acyclic acetal groups, e.g. $C_2$-$C_{20}$-alkoxymethoxy, preferably $C_2$-$C_9$-alkoxymethoxy, such as methoxymethoxy, ethoxymethoxy, n-propoxymethoxy, isopropoxymethoxy, n-butoxymethoxy, isobutoxymethoxy, sec-butoxymethoxy, tert-butoxymethoxy, n-hexyloxymethoxy and n-octyloxymethoxy; $C_3$-$C_{20}$-1-alkoxyethoxy, preferably $C_3$-$C_{10}$-1-alkoxyethoxy, such as 1-methoxyethoxy, 1-ethyoxyethoxy, 1-n-propoxyethoxy, 1-isopropoxyethoxy, 1-n-butoxyethoxy, 1-isobutoxyethoxy, 1-sec-butoxyethoxy, 1-tert-butoxyethoxy, 1-n-hexyloxyethoxy and 1-n-octyloxyethoxy; cyclic acetal groups, in particular those having 5 or 6 ring members, such as 2-furanyl, 2-tetrahydrofuranyl, 2-pyranyl, 2-tetrahydropyranyl, 1,3-dioxan-2-yl, 1,3-dioxan-4-yl and 1,4-dioxan-2-yl.

The novel compounds I are prepared by reacting an aldehyde of the formula II

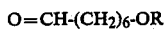    II where R is one of the abovementioned base-stable alcohol protective groups, with acetylene in an aprotic organic solvent in the presence of a base and, if required, then eliminating the protective group.

Hydroxyheptanals and their protected derivatives II are known or can be prepared by a conventional method, for example by hydroformylation of protected ω-hex-1-enols, such as 6-tert-butoxyhex-1-ene or 6-trimethylsilyloxyhex-1-ene, in the presence of a rhodium-triphenylphosphine complex as a catalyst, an excess of triphenylphosphine advantageously being used. Preferred conditions are temperatures of 0–150° C., in particular 20–60° C., a synthesis gas pressure of 50–200 bar and an inert organic solvent, such as a hydrocarbon or an ether, e.g. tetrahydrofuran, as the solvent.

From 1 to 10 moles of acetylene may be used per mole of II.

Examples of suitable solvents are hydrocarbons, such as benzene, toluene, xylene, petroleum ether or pentane, and ethers, such as diethyl ether, methyl tert-butyl ether or tetrahydrofuran. The amount of solvent is in general from 1 to 2 l per mole of II.

The reaction is carried out according to the following equation:

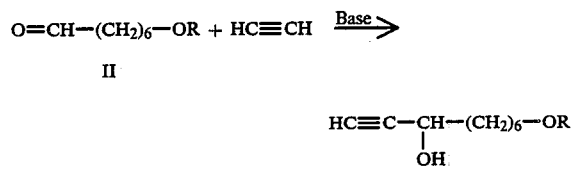

To prepare the 3,9-dihydroxynonyne, the alcohol protective groups can be eliminated in a conventional manner (cf. for example T. W. Greene, Protective Groups in Organic Synthesis, John Wiley, N.Y. 1981).

Suitable bases are compounds which are capable of deprotonating acetylene, for example Grignard compounds, e.g. alkyl- or alkenylmagnesium halides, such as methylmagnesium bromide, methylmagnesium iodide, vinylmagnesium bromide or ethylmagnesium chloride, or alkali metal amides, such as $LiNH_2$ or $NaNH_2$. As a rule, from 0.5 to 1, in particular 0.5, mole of base can be used per mole of acetylene. The reaction temperatures are in general from 0 to 50° C., in particular from 0 to 20° C.

The reaction mixture is worked up in a conventional manner, for example with water.

The reaction product can be purified, for example by distillation or chromatography, or can be used for subsequent stages without purification. If it is intended to liberate the 9-OH function in the protected derivative I, the general procedure described in, for example, T. W. Greene, Protective Groups in Organic Synthesis, John Wiley, N.Y., 1981, is followed. As a rule, however, the protective derivatives are further used.

The novel compounds I can be converted by a Meyer-Schuster rearrangement reaction (Houben-Weyl, Methoden der Organischen Chemie, Vol. VII/2, pages 907–927, 1973) into the known nonenals III unprotected or protected at the OH function, in accordance with the following equation

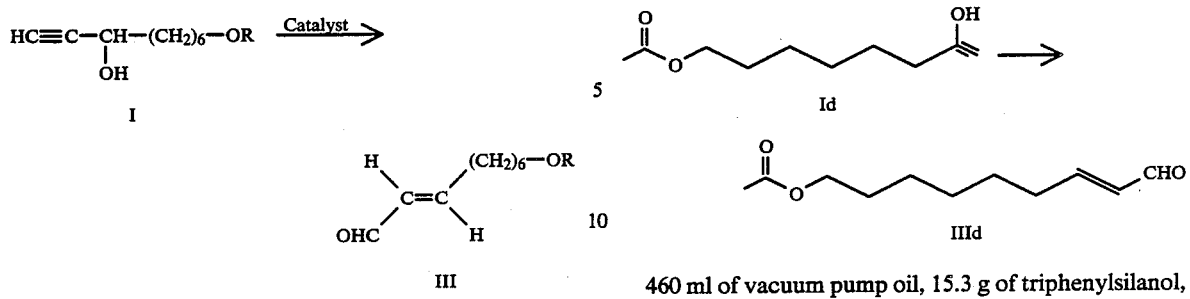

The use of these nonenals III for the synthesis of the desired pheromone active ingredient presents no problems and is described in GB-A-2 098 609 or Liebigs Ann. Chem. (1981), 1705-1720.

The Examples which follow illustrate the process:

(A) General method for the preparation of the acetylene alcohols Ia–Ie 3 moles of acetylene are passed, in the course of 2 hours, into 1 l of a 1.5 molar vinylmagnesium halide solution while cooling with ice. 1 mole of aldehyde is then added dropwise, after which stirring is continued at room temperature for about 1–2 hours.

To work up the mixture, 150 ml of $H_2O$ are added dropwise and the resulting magnesium salt is filtered off under suction. The filtrate is evaporated down in a rotary evaporator and methyl tert-butyl ether is added to the residue. The ether solution is washed with NaCl solution and then evaporated down, and the residue is distilled.

If desired, the crude product can also be used for the subsequent rearrangement reaction, without prior distillation.

Table 1 shows the physical and spectroscopic data of the acetylene alcohols Ia–Ie prepared by the above general method. All acetylene alcohols can be prepared in yields of 75–90%.

The shifts stated are based on tetramethylsilane (TMS) ($\delta TMS = 0$ ppm).

460 ml of vacuum pump oil, 15.3 g of triphenylsilanol, 8.3 g of tris-(triphenylsilyloxy)-vanadium oxide, 0.82 g of benzoic acid and 95.1 g (0.46 mole) of Id are stirred for 4 hours at 140° C.

The reaction product and unconverted starting material are then subjected to fractional distillation through a column under reduced pressure from an oil pump. Distillation gave $\alpha,\beta$-unsaturated aldehyde which was pure according to NMR spectroscopy, the yield of isolated product being 65%. The unconverted starting material could readily be used for a further rearrangement reaction.

The acetylene alcohols Ia–Ic and Ie were subjected to a rearrangement reaction in a similar manner to give the corresponding $\alpha,\beta$-unsaturated aldehydes, the yields of isolated products being 53–79%.

(C) Preparation of the starting materials ($C_1$) $CH_2=CH-(CH_2)_4-OH \rightarrow CH_2=CH-(CH_2)_4-O-C(CH_3)_3$ 200 g of hex-1-en-6-ol are dissolved in 250 ml of methyl tert-butyl ether, and 100 g of acidic ion exchanger (SPC 118H+) are added. Isobutylene is then passed in until the solution is saturated, and the reaction is monitored by thin layer chromatography, After 4 hours, the reaction is complete. Fractional distillation gives 243 g of 6-tert-butoxyhex-1-ene having a gas chromatographic purity of 98.5%; bp.: 66–67° C./32 mbar. Yield: 75% of theory.

($C_2$) Preparation of protected 7-hydroxyheptanals (II) by hydroformylation

TABLE 1

3,9-Dihydroxynonyne Dihydroxynonyne and its derivatives protected at the 9-OH function

| Example | R | bp. [°C./mbar] | $^1$H-NHR (CDCl$_3$) $\delta$ (ppm)[a] | $^{13}$C-NMR-(CDCl$_3$) $\delta$ (ppm)[a] |
|---|---|---|---|---|
| Ia | H | 108–120/0.27 | 4.35(t, 1H); 3.60(t, 2H) 2.45(s, 1H); 1.20–1.75(11H); | — |
| Ib | (tetrahydropyranyl) | 130–150/0.04 | 4.59(1H); 4.32(t, 1H); 3.86(m, 1H); 3.70(m, 1H); 3.42–3.58(m, 2H); 2.47(s, 1H); 1.25–1.90(m, 17H) | 98.7; 85.6; 72.2; 67.5; 62.0; 61.9; 37.7; 30.8; 29.7; 29.1; 26.2; 25.6; 25.1; 19.5 |
| Ic | tert-butyl | 86–89/0.5 | 4.32(t, 1H); 3.32(t, 1H); 3.05(OH); 2.47(s, 1H); 1.30–1.76(m, 10H); 1.18(s, 9H) | 85.6; 72.6; 62.0; 61.6; 37.8; 30.7; 29.2; 27.7; 26.2; 25.1 |
| Id | COCH$_3$ | 106–120/0.33 | 4.37(t, 1H); 4.07(t, 2H); 2.75(OH); 2.48(s, 1H); 2.07(s, 3H); 1.27–1.80(m, 10H) | 171.2; 85.6; 72.6; 64.6; 62.0; 37.7; 28.9; 28.6; 25.9; 25.0; 20.8 |
| Ie | Si(CH$_3$)$_3$ | 87–92/0.1 | 4.28(t, 1H); 3.49(t, 2H); 3.40(s, 1H); 2.35(s,1H); 1.70–1.10(10H); 0.15(s, 9H) | 85.9; 73.0; 63.1; 62.3; 38.1; 33.0; 29.5; 26.2; 25.2; -0.4 |

[a]internal standard = TMS (B) Preparation method for the rearrangement of the acetylene alcohol Id to give the corresponding $\alpha,\beta$-unsaturated aldehyde IIId 1,190 g of 6-tert-butoxyhex-1-ene in 800 g of tetrahydrofuran are hydroformylated in the presence of 1.5 g of Rh(Co)H(PO$_3$)$_3$ and 45 g of triphenylphosphine at 50° C. with synthesis gas (CO: H$_2$=1:1) under a pressure of 100 bar for 12 hours and then at 60° C./150 bar for a further 12 hours. Distillation of the reacted mixture gives 121 g of unconverted alkene as well as 1,009 g of an aldehyde mixture having a boiling point of 62–77° C. under 2 mbar. In addition to 46.5 g of catalyst, about 70 g of high boilers or polymers remain as the distillation residue. Fractionation of the 1,009 g of aldehyde mixture is carried out over a 160 cm packed column under 20 mbar. The desired straight-chain aldehyde (7-tert-butoxyheptanal) is obtained in a purity of 99.6% (boiling point 116° C./20 mbar) and the branched 2-methyl-6-tert-butoxyhexanal is obtained in a purity of 99.7% (boiling point 110–112° C./20 mbar). Yield: 650 g of 7-tert-butoxyheptanal in addition to 280 g of 2-methyl-6-tert-butoxyhexanal.

For example, the corresponding trimethylsilyl-protected aldehyde can be prepared in a similar manner.

We claim:
1. 3,9-Dihydroxynonyne or its derivative protected at the 9-OH function, of the formula I

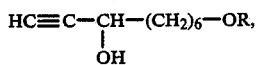

where R is hydrogen or a base-stable alcohol protective group.

2. 3,9-Dihydroxynonyne or its derivative as claimed in claim 1, wherein R is a tertiary $C_4$-$C_{20}$-alkyl group, a $C_3$-$C_{20}$-trialkylsilyl group, benzyl, benzoyl, $C_2$-$C_{10}$-alkansyl, or an acyclic or cyclic acetal group.

* * * * *